(12) United States Patent
Remiszewski et al.

(10) Patent No.: US 6,446,854 B1
(45) Date of Patent: Sep. 10, 2002

(54) SURGICAL STAPLING APPARATUS

(75) Inventors: Stanley H. Remiszewski, Greenwich; David T. Green, Westport; Henry Bolanos, East Norwalk, all of CT (US)

(73) Assignee: United States Surgical Corporation, Norwalk, CT (US)

( * ) Notice: Subject to any disclaimer, the term of this patent is extended or adjusted under 35 U.S.C. 154(b) by 1465 days.

(21) Appl. No.: 08/651,502

(22) Filed: May 22, 1996

Related U.S. Application Data

(63) Continuation of application No. 08/396,083, filed on Feb. 28, 1995, now abandoned, which is a continuation of application No. 08/196,891, filed on Feb. 15, 1994, now abandoned, which is a continuation of application No. 08/005, 205, filed on Jan. 15, 1993, now abandoned, which is a continuation of application No. 07/778,785, filed on Oct. 18, 1991, now abandoned.

(51) Int. Cl.$^7$ ............................................. A61B 17/068
(52) U.S. Cl. .................... 227/175.1; 227/19; 227/176.1
(58) Field of Search ................. 227/19, 175.1, 227/176.1, 177.1, 178.1, 179.1, 180

(56) References Cited

U.S. PATENT DOCUMENTS

| | | | | |
|---|---|---|---|---|
| 960,300 A | * | 6/1910 | Fischer | 227/19 X |
| 2,301,622 A | * | 11/1942 | Hambrecht | 227/177 |
| 2,853,074 A | * | 9/1958 | Olson | 227/19 |
| 2,874,384 A | * | 2/1959 | Krone | 227/19 |
| 2,965,900 A | * | 12/1960 | Inokouchi | 227/19 |
| 3,144,654 A | * | 8/1964 | Mallina et al. | 227/19 |
| 3,269,631 A | * | 8/1966 | Takaro | 227/19 X |
| 3,278,107 A | | 10/1966 | Rygg | |
| 3,314,581 A | * | 4/1967 | Kapitanov et al. | 227/19 X |
| 3,604,561 A | | 9/1971 | Mallina et al. | |
| 4,290,542 A | * | 9/1981 | Fedotov et al. | 227/19 X |
| 4,565,199 A | | 1/1986 | Becht | |
| 4,566,620 A | * | 1/1986 | Green et al. | 227/19 |
| 4,591,085 A | * | 5/1986 | Di Giovanni | 227/19 X |
| 4,591,086 A | | 5/1986 | Campbell et al. | |
| 4,633,874 A | * | 1/1987 | Chow et al. | 227/19 X |
| 4,944,443 A | | 7/1990 | Oddsen et al. | |
| 4,991,763 A | | 2/1991 | Storace | |
| 5,040,715 A | * | 8/1991 | Green et al. | 227/21 X |
| 5,071,052 A | * | 12/1991 | Rodak et al. | 227/19 X |
| 5,137,198 A | * | 8/1992 | Nobis et al. | 227/19 |
| 5,366,134 A | * | 11/1994 | Green et al. | 227/176 |

FOREIGN PATENT DOCUMENTS

| | | | | |
|---|---|---|---|---|
| DE | 2341596 | | 4/1975 | |
| EP | 0092300 | | 10/1983 | |
| EP | 0389238 | | 9/1990 | |
| FR | 2443238 | | 7/1980 | |
| GB | 319886 | | 10/1929 | |
| GB | 2065536 | * | 7/1981 | 227/176 |
| GB | 2092503 | | 8/1982 | |

* cited by examiner

*Primary Examiner*—Boyer Ashley

(57) ABSTRACT

A surgical stapling apparatus having first and second handle members pivotably mounted to one another for movement from an open position to a closed position to clamp body tissue between the distal jaws. After the body tissue is clamped, a trigger mechanism is activated to advance a staple pusher to force a staple through the tissue and into contact with an anvil to deform the staple legs. An actuating lever may be interposed between the trigger mechanism and the staple pusher.

31 Claims, 15 Drawing Sheets

SURGICAL STAPLING APPARATUS

This is a continuation, of application Ser. No. 08/396,083 filed on Feb. 28, 1995, now abandoned, which is a continuation of application Ser. No 08/196,891 filed on Feb. 15, 1994, now abandoned, which is a continuation of Ser. No. 08/005,205 filed on Jan. 15, 1993, now abandoned, which is a continuation of Ser. No. 07/778,785 filed on Oct. 18, 1991, now abandoned.

BACKGROUND OF THE INVENTION

1. Field of the Invention

This invention relates to a surgical stapling apparatus, and more particularly to an apparatus for clamping vascular tissue and subsequently driving an individual staple through the tissue and into contact with a staple forming anvil.

2. Description of the Related Art

Surgical apparatus for applying clips to vascular tissue are well known in the art. In these devices, each leg of the clip, typically U-shaped in configuration, is held in one of the opposing jaws of the instrument and the jaws are placed on sides of the vessel. The jaws are then closed to flatten the clip to squeeze the vessel walls together to effect hemostasis. These prior apparatus suffer from the disadvantage that the clip can only be advanced into the jaws of the instrument when the jaws are open so that vessel clamping and clip closing occur simultaneously. As a result, the surgeon cannot first ensure the vessel is properly clamped before committing to clip closure. Another disadvantage of these clip appliers is they can only be utilized to close a single vessel since they straddle the vessel; they cannot be used to attach approximated vessels or vessel portions.

Another prior method for repairing vascular tissue is suturing. Although two approximated vessels can be attached by this method, it is not only time consuming, but is difficult to accomplish in certain procedures, especially when the vessel is not in an easily accessible location or when microvascular tissue is involved. Still another disadvantage of suturing is that numerous punctures are made in the vessel walls since a hole is created with each passage of the suture needle.

Instruments for applying single staples one at a time to body tissue are also known. These instruments differ from the clip appliers in that they provide one jaw which contains a staple and an opposing jaw which contains an anvil for deforming the legs of the staple. For example, U.S. Pat. No. 3,278,107 discloses a device where closing of the handles clamps the vessels and forms a single staple. This instrument suffers from the disadvantage associated with the above described clip appliers since clamping of the tissue and application of the staple occur simultaneously. U.S. Pat. No. 3,604,561 also discloses a stapler having a pair of clamping jaws and a mechanism for advancing the staple into an anvil. When sufficient force is applied to the handles, the staple is driven through the tissue and into the anvil. This instrument is deficient in that premature firing could occur if too much force is applied to the handles during the initial clamping action.

The need therefore exists for an improved surgical stapler which can apply staples one at a time to body tissue such as vascular tissue and in which premature firing of the staples, e.g. firing before the tissue is satisfactorily clamped, is prevented. Such an instrument could be utilized for closing individual vessels as well as attaching approximated vessels.

SUMMARY OF THE INVENTION

The present invention overcomes the deficiencies and disadvantages of the prior art by providing a surgical stapling apparatus comprising a first handle member with an elongated jaw at its distal end having a plurality of staples positioned thereon and a second handle member comprising a second elongated jaw at its distal end having an anvil positioned thereon. The two handles are pivoted in scissor-like fashion to move the jaws to a closed position to clamp body tissue therebetween. Trigger means, independent of the pivoting means for closing the handles, actuates the staple pusher means to advance a single staple through the tissue and into contact with an anvil. The trigger means may be slidably mounted proximally of the pusher means for movement between a rest position and a biased position to pivot the pusher means. In one embodiment the trigger means is connected directly to the pusher means. In an alternate embodiment, an actuating lever can connect the trigger means to the pusher means. The actuating lever may include a cam slot which receives a pin extending from the trigger means so that proximal movement of the trigger means causes the pin to pivot the actuating lever as it travels in the cam slot. The actuating lever preferably includes an inwardly extending member which is received in a channel of the pusher means to pivot the pusher means into engagement with the staple.

An interlocking mechanism may be provided to prevent pivotal movement of the actuating lever unless the instrument jaws are closed. The interlocking mechanism may be in the form of a slidably mounted locking pin engaging a cut-out portion of the actuating lever.

The staple advancing means may be movable in the direction which is at an angle to the longitudinal axis of the anvil jaw. A removable staple cartridge can be provided containing a plurality of staples which are also angled with respect to the longitudinal axes and are fed one at a time into the firing path of the staple advancing means.

BRIEF DESCRIPTION OF THE DRAWINGS

Preferred embodiments of the invention are described hereinbelow with reference to the drawings, wherein.

DETAILED DESCRIPTION OF THE PREFERRED EMBODIMENTS

Figure 1:
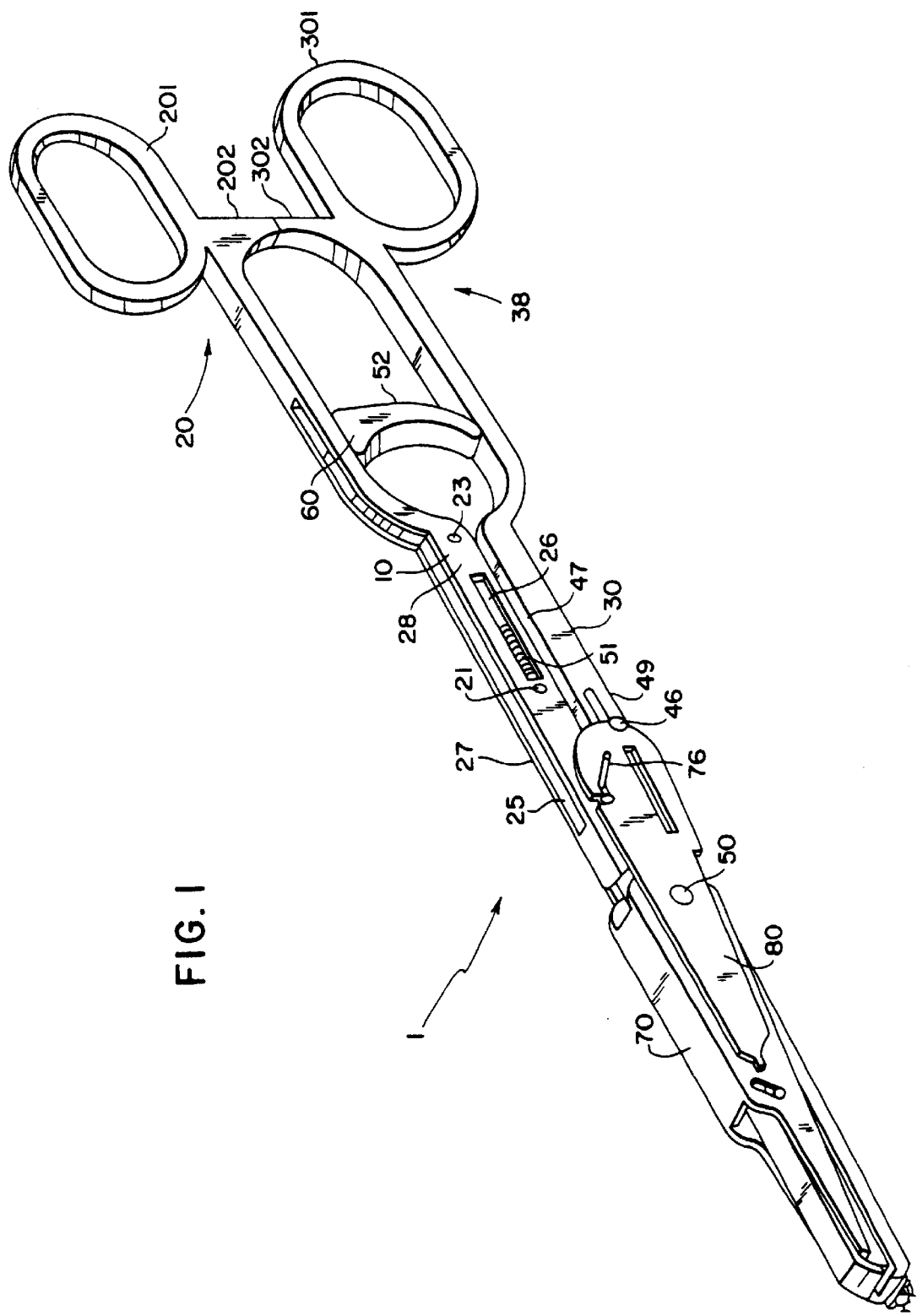
FIG. 1 is a side perspective view of one embodiment of the surgical stapling apparatus of the present invention.

Referring now the drawings, wherein like reference numerals represent identical parts throughout the several views, FIGS. 1–9 illustrate a first embodiment and FIGS. 10–16 illustrate a second embodiment of the surgical apparatus of the present invention. In both embodiments, the instrument handles are pivotally mounted to each other and terminate in tissue clamping jaws for gripping body tissue, such as vascular tissue, therebetween. Once the body tissue is clamped, the staple pusher mechanism can be actuated to drive a staple through the tissue and against an anvil for formation into a B-shaped configuration.

Figure 2:
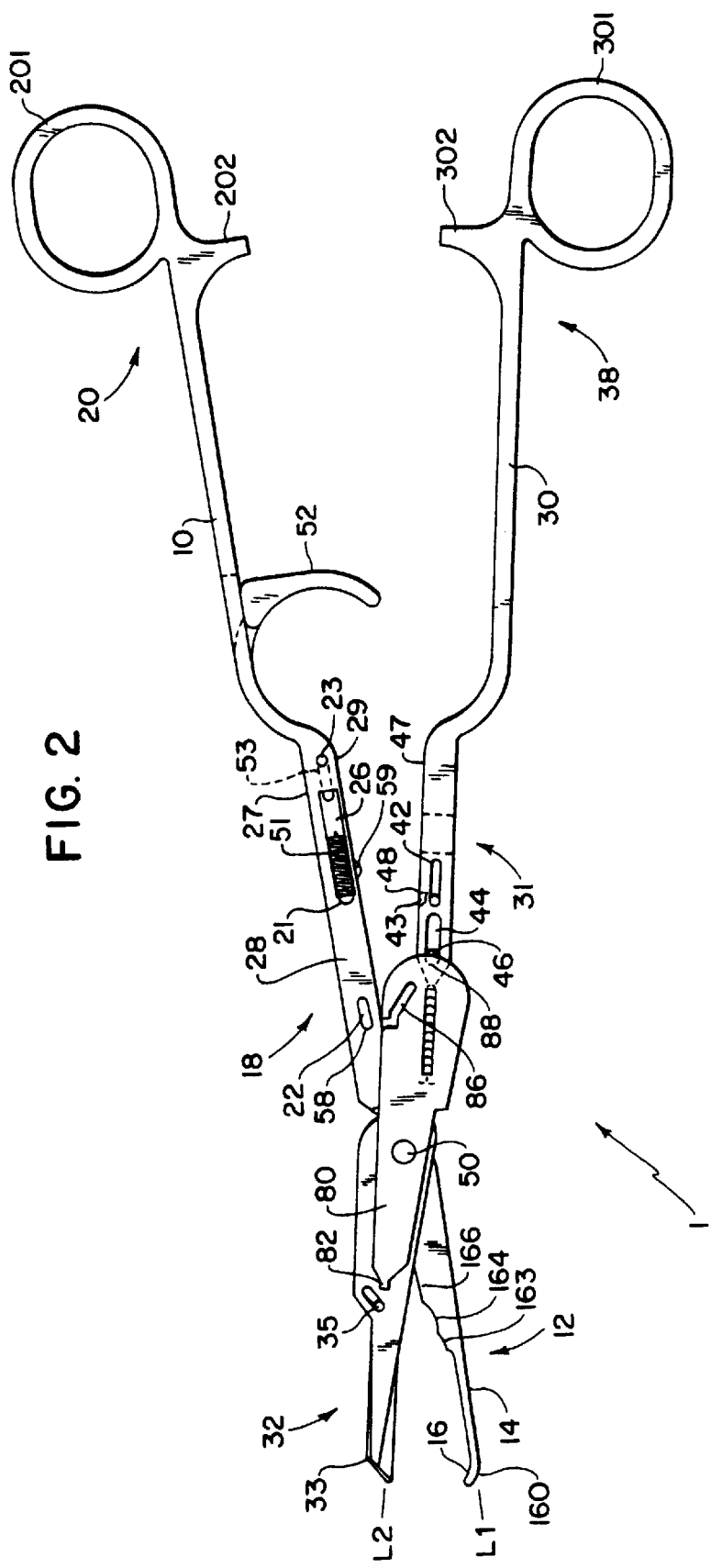
FIG. 2 is a side view of the apparatus of FIG. 1 shown with the tissue clamping jaws in the open position.
Figure 3:
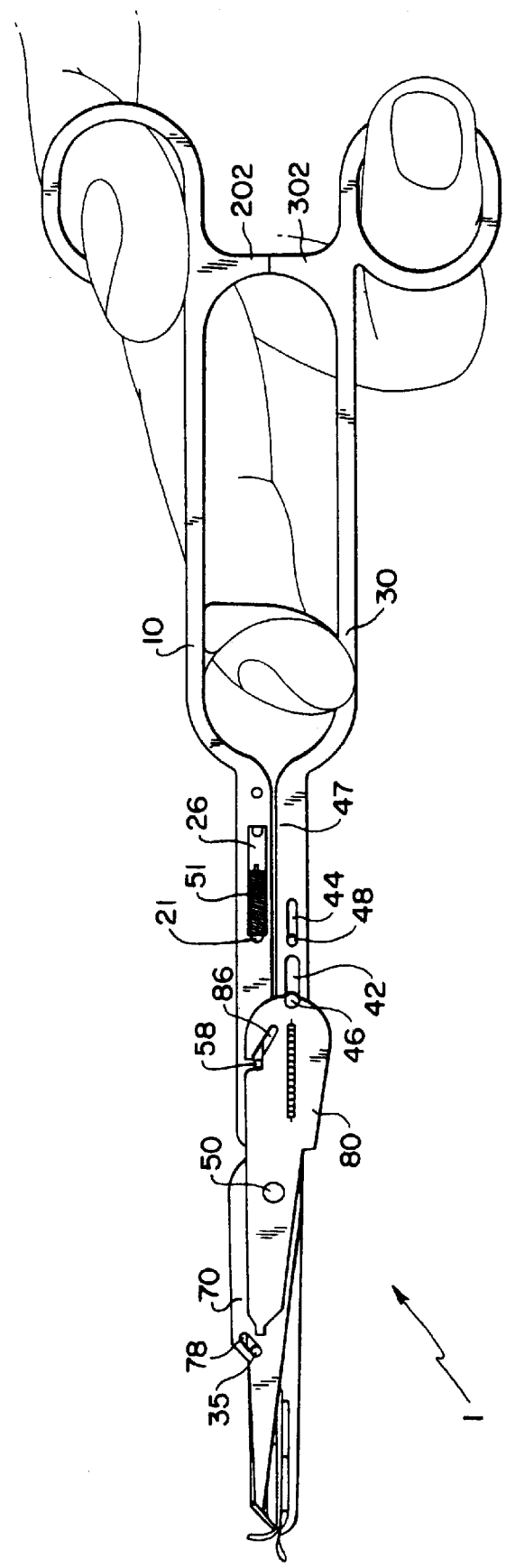
FIG. 3 is a side view of the apparatus shown with the tissue clamping jaws in the closed position and the staple pusher in the retracted, pre-fired position.

Turning first to the embodiment of FIG. 1, instrument 1 comprises an elongated anvil carrying arm or handle 10 and an elongated staple carrying arm or handle 30 mounted to each other in scissor-like fashion via a central guide fastener 50. Guide fastener 50 is supported by a pivot bushing (not shown) which allows handles 10 and 30 to be pivoted between an opened position as shown in FIG. 2 and a closed position as shown in FIG. 3. Instrument 1 also includes a staple pusher 70 for advancing staples one at a time into body tissue, an actuating lever 80 for activating staple pusher 70, and a trigger mechanism 60 for driving actuating lever 80.

Figure 8:
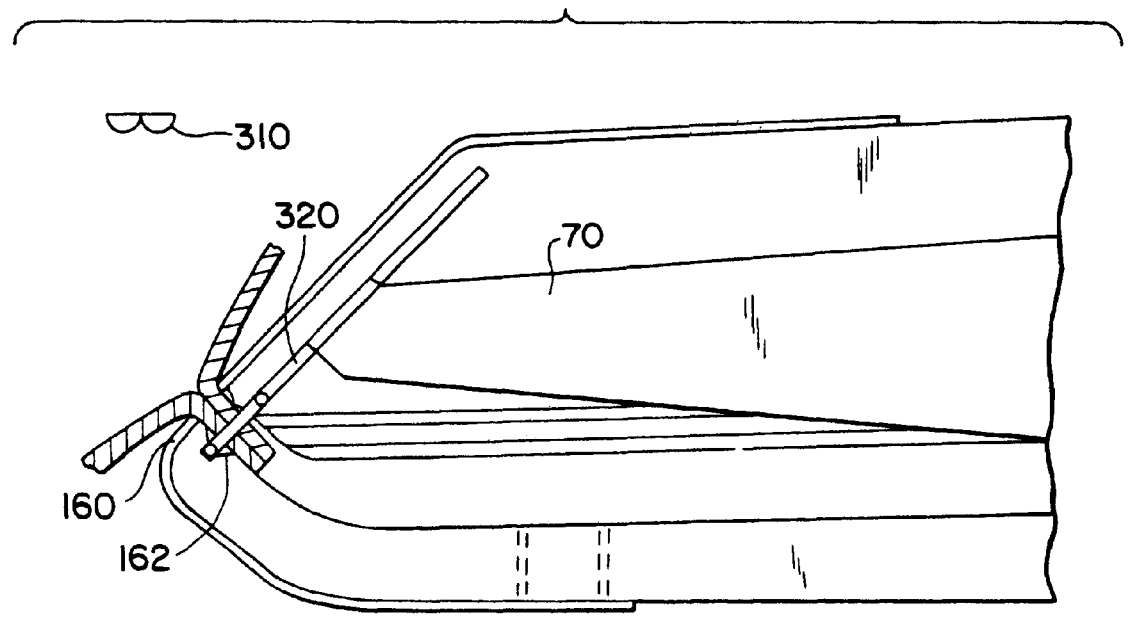
FIG. 8 is an enlarged side view of the distal end of the apparatus showing a staple implanted in the body tissue and the staple pusher partially returned to its retracted position.

An elongated anvil jaw 14, preferably integral with handle 10, is formed on the distal portion 12 of anvil carrying arm 10 and includes an anvil portion 16 having an inclined wall 160 forming an obtuse angle with the longitudinal axis L1. The inclined wall 160 may optionally include a widened width portion and may terminate in a pair of tissue prongs (not shown) to prevent tissue from entering the instrument during use and interfering with the driving and formation of the staple. A pair of depressions 162, only one of which is shown in the drawings, is formed in inclined wall 160 and configured to receive one of the staple legs 310 for deforming it around body tissue to assume a B-shaped configuration as shown in FIG. 8. Anvil jaw 14 is illustratively stepped to form surfaces 163, 164 and 166 (FIG. 2) of differing heights to cooperate with the staple carrying jaw of arm 30.

Referring to FIGS. 1 and 2, central portion 18 of anvil 10 has a longitudinal opening 25 extending through upper wall 27 and lower wall 29 to receive trigger mechanism 60. An elongated recess 26 is formed in inner side wall 28, aligning with longitudinal guide slot 54 of trigger mechanism 60 to accommodate the trigger mechanism tension spring 51, and distal pin 21 secures one end of this spring. Fixed proximal pin 23 and longitudinal slot 222 cooperate with the trigger mechanism in a manner described below.

Proximal portions 20 and 38 of elongated handles 10, 30 terminate in finger loops 201, 301, respectively, to receive the user's fingers to facilitate manipulation of the instrument. Inwardly extending stops 202, 302, of anvil carrying handle 10 and staple carrying handle 30 are configured to come into abutment when the handles are pivoted a predetermined distance corresponding to the maximum desired closure of anvil jaw 14 and staple jaw 33 for clamping the vessel. Consequently, overclamping is prevented.

Figure 9:
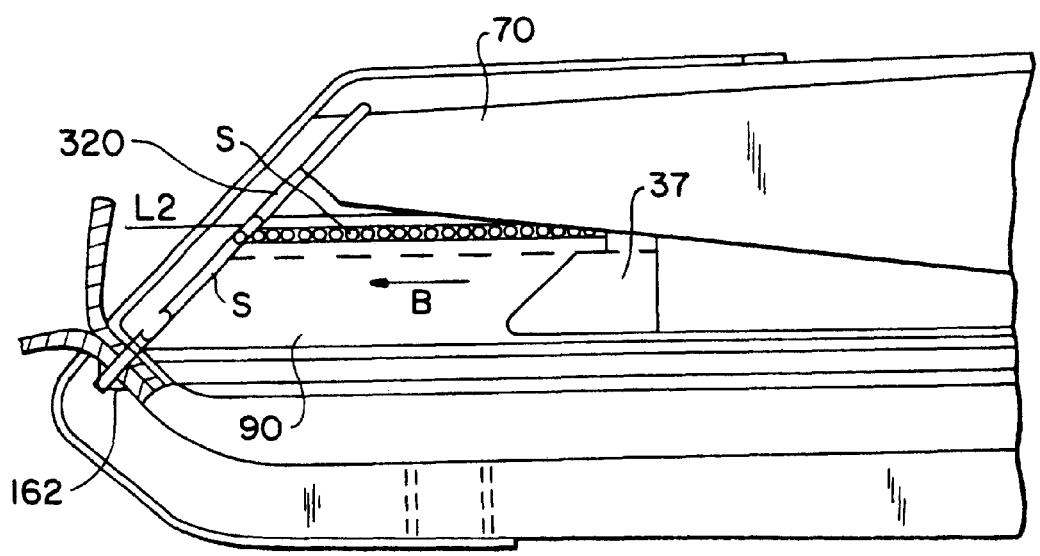
FIG. 9 is an enlarged side view of the distal end of the apparatus showing a staple implanted in the body tissue and the staple pusher fully returned to its retracted position.
Figure 10:
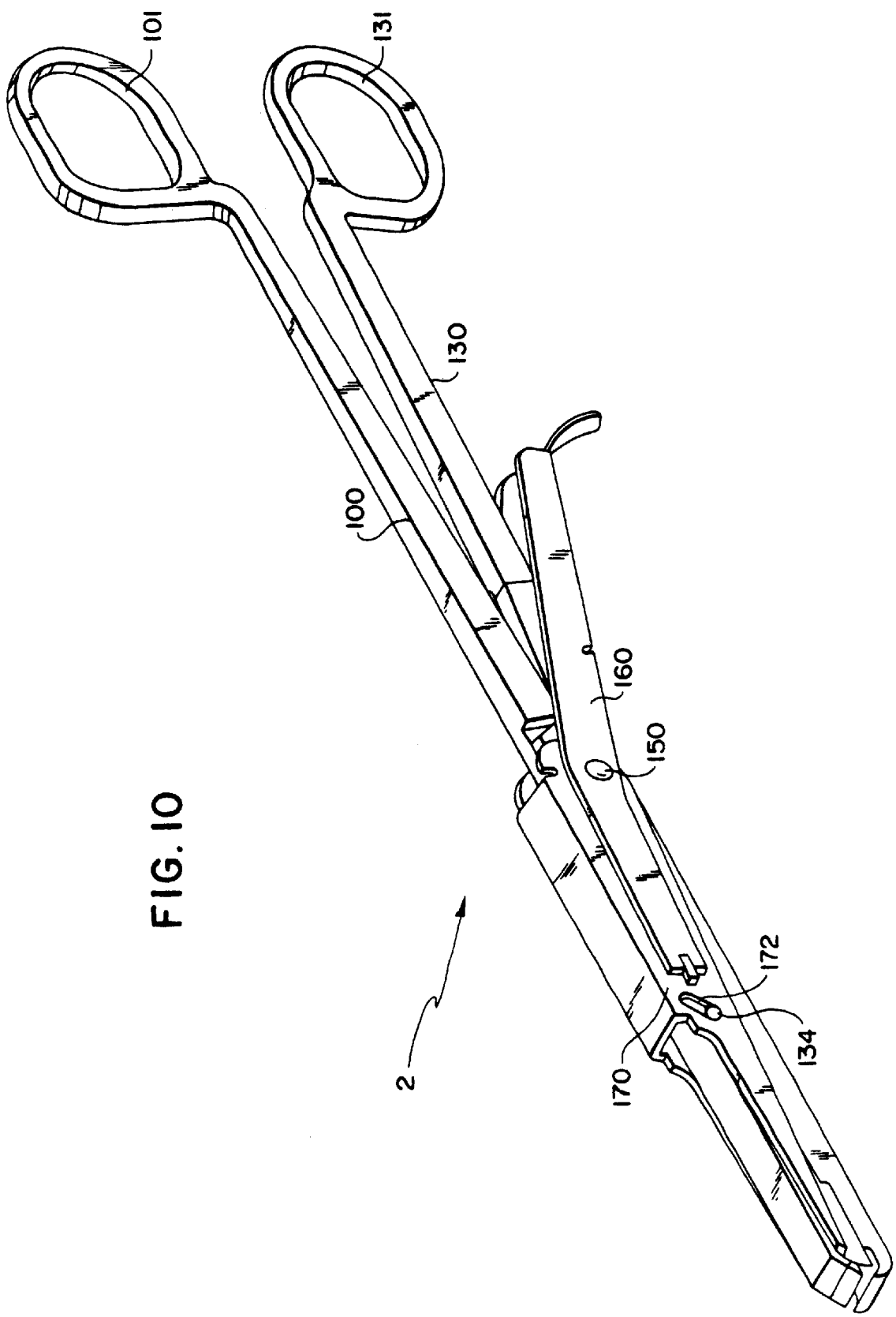
FIG. 10 is a side perspective view of an alternate embodiment of the surgical stapling apparatus of the present invention.

Staple jaw 33, formed at a distal portion 32 of staple carrying handle 30, mounts a staple cartridge containing a plurality of staples "S". The staples S are aligned in a direction parallel to the longitudinal axis L2 of staple jaw 33 with the staple legs positioned at an angle to axis L2, as best shown in FIG. 9. A spring biased stack pusher 37 is positioned in the staple cartridge abutting the proximalmost staple to urge the stack of staples distally so the staples S can be fed one at a time into the path 320 of staple pusher 70 for ejection into the body tissue. A transverse guide pin 35 (FIG. 2) extends from staple jaw 33 to cooperate with staple pusher 70 to restrict longitudinal movement thereof The staple cartridge 91 is retained within top rails 92 of cartridge holder 90, shown in FIGS. 6A and 6B. Dowel 93 and mounting fastener 98 secure the staple cartridge and the holder 90 to staple jaw 33. Front wall 95 is angled inwardly to provide a guide path for the staple pusher 70 as it pushes a staple downwardly through narrow channel 96. The staple cartridge can optionally be removably mounted to the instrument so that it can be removed and replaced by a loaded cartridge containing the same or different sized staples.

Figure 4:
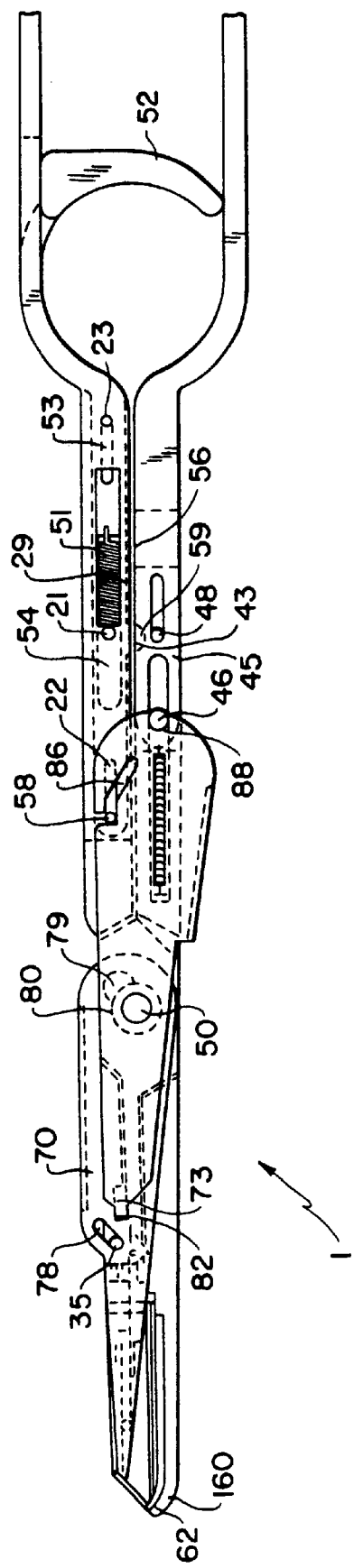
FIG. 4 is a side view of the apparatus similar to FIG. 3 showing the internal components of the apparatus.

Referring back to FIGS. 1–4, central portion 31 of staple carrying handle 30 has a longitudinal opening formed through its top wall 47 and bottom wall 49 to receive a reciprocating safety plate 45. Safety plate 45, as best shown in FIGS. 4 and 5B, has a safety pin 46 extending through side wall slot 44 and an alignment pin 48 extending through side wall slot 42. Safety pin 46 engages actuating lever 80 to prevent pivotal movement thereof before the tissue is properly clamped. Safety plate 45 also includes an upper depression 43 which cooperates with trigger mechanism 60 only when the handles are closed.

Figure 5A:
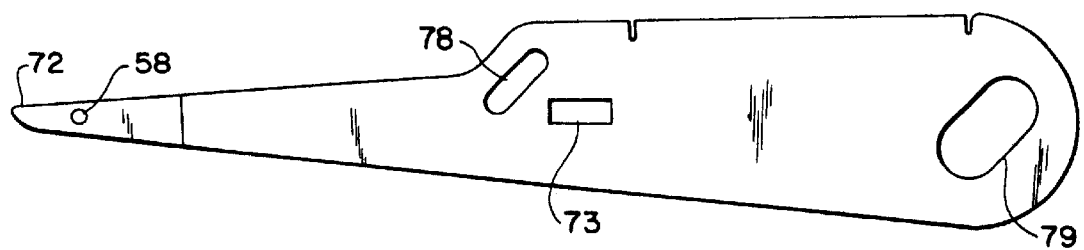
FIG. 5A is an enlarged side view of the staple pusher of the apparatus.
Figure 5B:
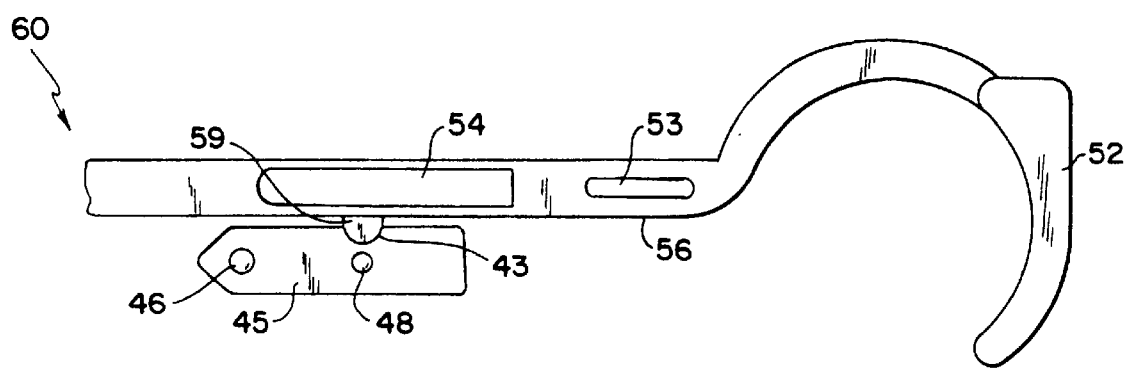
FIG. 5B is an enlarged side view of the trigger mechanism of the apparatus.
Figure 6A:
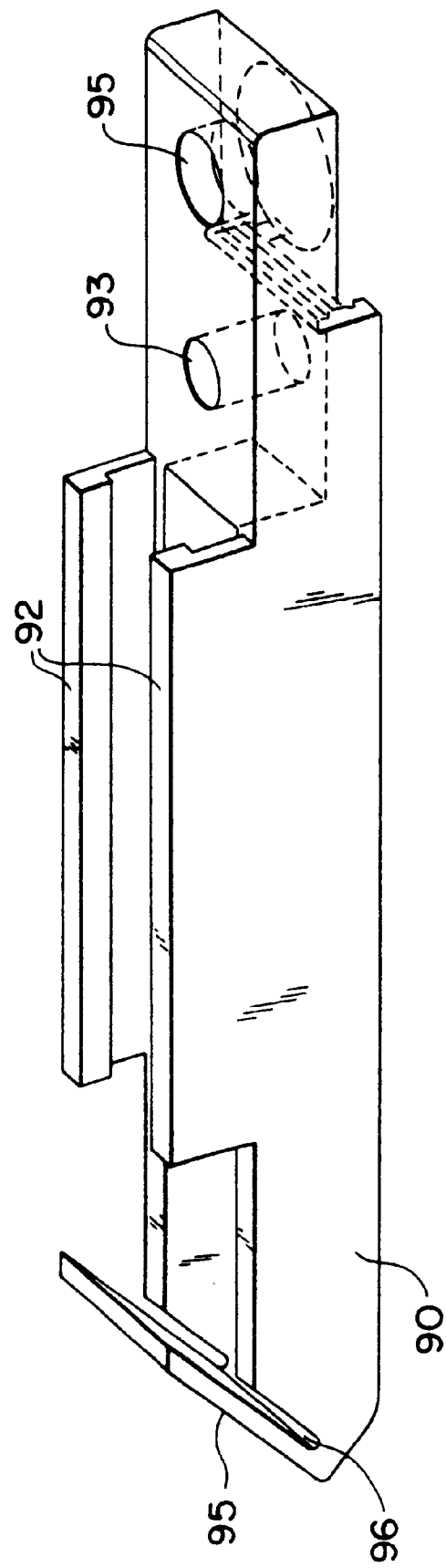
FIG. 6A is an enlarged side perspective view of the staple cartridge holder.
Figure 6B:
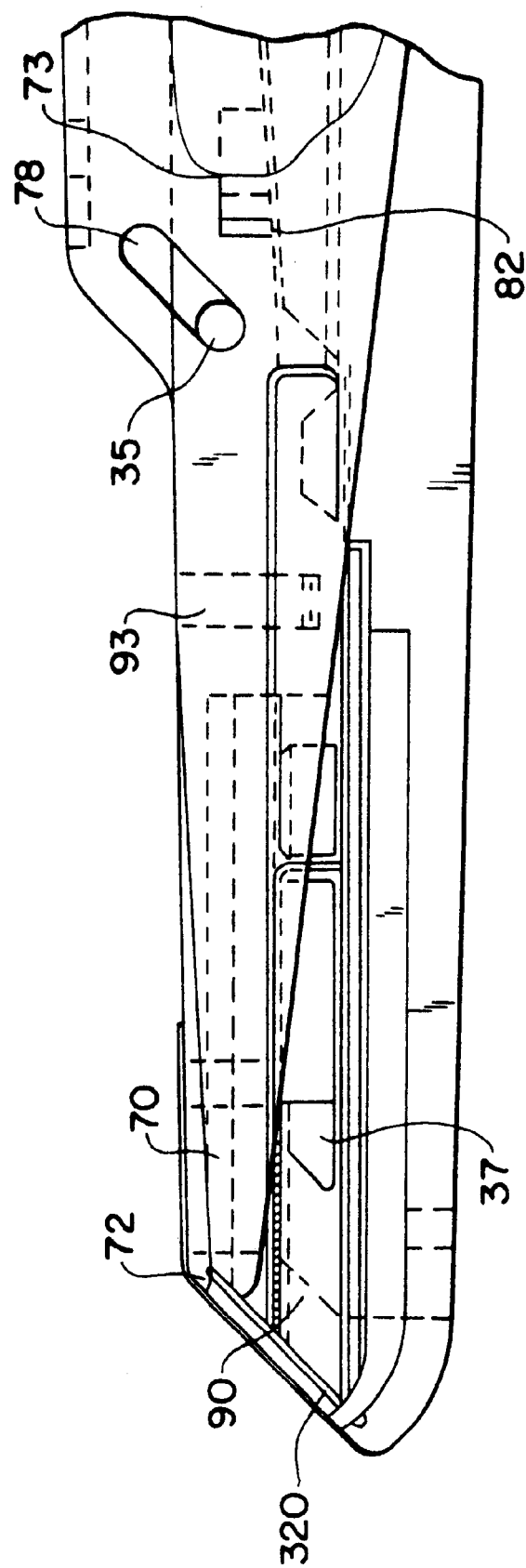
FIG. 6B is an enlarged side view showing the staple cartridge mounted in the apparatus.

Turning now to the staple pusher mechanism 70, and with particular reference FIG. 4 and to FIG. 5A which illustrates an enlarged view, staple pusher 70 is attached to anvil and staple carrying handles 10 and 30 by guide fastener 50 extending through guide slot 79. Staple pusher 70 includes a finger 72 at its distal end having a staple engaging surface which contacts a crown portion of the distalmost staple and advances it into the body tissue. Finger 72 is preferably T-shaped in configuration. Pusher mechanism 70 is linked to trigger mechanism 60 by actuating lever 80 and mounted for sliding movement between a retracted position, spaced from the anvil jaw 14 as in FIG. 4, to an advanced position adjacent the anvil jaw 14 as in FIG. 7. A diagonal slot 78, positioned at an angle to the longitudinal axis L2, has a camming surface to allow for sliding movement along transverse guide pin 35 of anvil jaw 33. Longitudinally extending channel 73 is configured to receive a portion of actuating lever 80 such that pusher 70 translates on guide pin 35 and fastener 50 when actuating lever 80 is pulled proximally by trigger mechanism 60.

Figure 7:
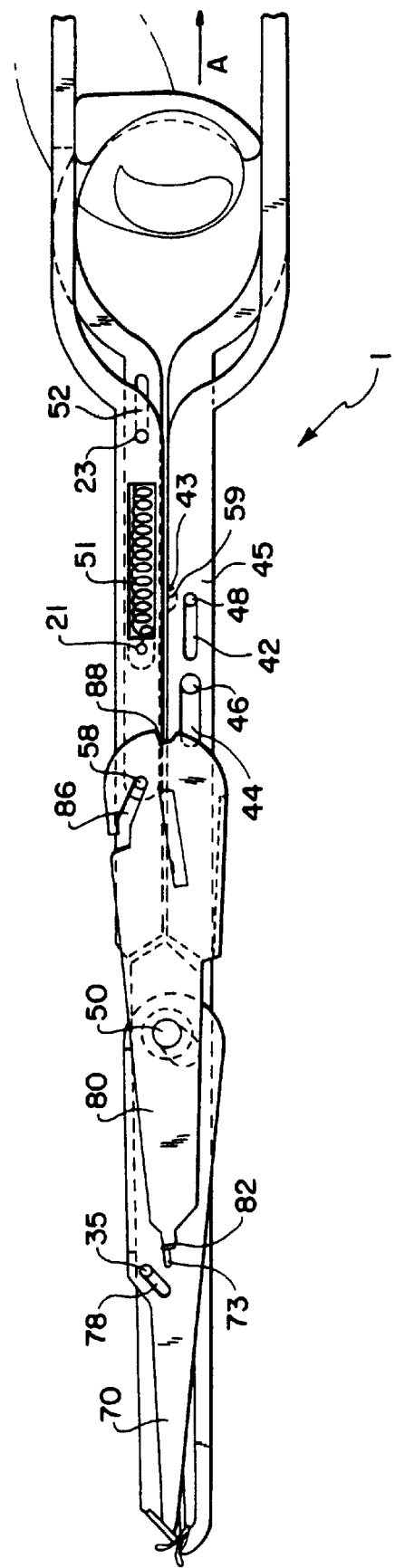
FIG. 7 is a side view of the apparatus and its internal components shown with the tissue clamping jaws in the closed position and the staple pusher in its advanced, fired position.

Actuating lever 80 is pivotably mounted to both anvil carrying handle 10 and staple carrying handle 30 via central guide fastener 50 for movement between a relaxed distal position wherein pusher 70 is in a retracted position (FIG. 4), and a tensioned proximal position wherein pusher 70 is rotated to its advanced position (FIG. 7). As shown in FIG. 4, angular cam slot 86 has a horizontal surface portion and a diagonal surface portion to cooperate with a camming pin 58 of the trigger mechanism 60 to cause the rear end of actuating lever 80 to pivot upwardly and its front portion to pivot downwardly and proximally when trigger mechanism 60 is actuated. A locking groove 88 is formed in the rearmost end of actuating lever 80 to receive locking pin 46 of reciprocating plate 45 to prevent pivotal movement of actuating lever 80 until the jaws are closed and plate 45 is retracted as mentioned above.

Trigger mechanism 60 actuates lever 80 which in turn actuates pusher mechanism 70. Trigger mechanism 60 is sidably mounted in longitudinal opening 25 of anvil carrying handle 10, as shown in FIG. 1, for movement between a normal distal position (FIG. 4) and a retracted proximal position (FIG. 7). Tension spring 51, connected at one end to anvil carrying handle 10 via mounting pin 21 as noted above, and at its opposite end to trigger mechanism 60, biases trigger mechanism 60 to its distal position. An arcuate trigger arm 52, formed at the proximal end and positioned between handles 10, 30, is adapted to be grasped by the user. As best shown in FIGS. 4 and 5B, an interlock 59, preferably integral with trigger 50, extends below the lower wall 56 of trigger mechanism 60 as well as below the lower wall 29 of anvil carrying handle 10 to mate with upper depression 43 of plate 45 only when the jaws are pivoted to their closed, i.e. clamping, position. In this closed position, retraction of trigger mechanism 60 carries plate 45 proximally to disengage locking pin 46 from locking groove 88 to allow actuating lever 80 to pivot. However, if trigger mechanism 60 is activated before the handles are closed, safety plate 45 will not be engaged and retracted by the trigger mechanism and safety pin 46 will remain in locking engagement with actuating lever 80. Camming pin 58 extends transversely from trigger mechanism 60 through longitudinal slot 22 of anvil carrying handle 10 and engages angular cam slot 86 of actuating lever 80 to effect movement thereof as described above.

Turning now to the operation of the instrument, to separate anvil jaw 14 from staple jaw 33, the anvil carrying handle 10 and staple carrying handle 30 are pivoted to the open position shown in FIG. 2 by grasping and separating finger loops 201, 301. In this position, camming pin 58 of trigger mechanism 60 is out of engagement with angular cam slot 86 of actuating lever 80 and interlock 59 is spaced from upper depression 43 of reciprocating plate 46. Locking pin 46 of reciprocating plate 45, however, is engaged with locking groove 88 to prevent pivotal movement of actuating lever 80 and concomitant actuation of staple pusher 70.

The opened anvil and staple jaws 14, 33 are placed around the body tissue and the handles 10, 30 are pivoted toward each other in a scissor-like fashion to clamp the tissue as shown in FIG. 3. Stops 202 and 302 prevent overclamping of the vessel as their contact limits closing of the handles. Note that if the tissue is not properly clamped or the surgeon wishes to clamp the tissue at an alternative surgical site, since closing of the handles did not fire any staples, the surgeon can pivot the handles away from each other to reopen the jaws, move the jaws to the desired location and re-clamp the tissue.

Once the jaws 14, 33 are closed around the tissue, a staple can now be applied to the body tissue. In this closed, prefired position as shown in FIGS. 3 and 4, locking pin 46 remains engaged with locking groove 88, camming pin 58 is seated in the horizontal surface portion of angular cam slot 86, and interlock 59 is engaged with upper depression 43 of reciprocating plate 45.

The user actuates the firing mechanism by pulling trigger arm 52 proximally in the direction of arrow A of FIG. 7. This causes safety plate 45 to slide proximally due to its engagement with interlock 59 of trigger mechanism 60, thereby sliding locking pin 46 out of engagement with locking groove 88 to free actuating lever 80 for pivotal motion. Fixed proximal 23 cooperates with longitudinal guide slot 222 of trigger mechanism 60 to prevent non-longitudinal motion of trigger mechanism 60. This longitudinal sliding motion of trigger mechanism 50 is also transferred to pivotal motion of actuating lever 80 as camming pin 58 slides downwardly and rearwardly in the diagonal surface portion of angular cam slot 86.

Pivotal movement of actuating lever 80 is translated to sliding movement of pusher mechanism 70 along guide pin 35 and guide fastener 50 due to the engagement of inwardly extending distal finger 82 and channel 73. Pusher 70 is forced downwardly towards anvil carrying arm 10, with the camming surface of diagonal slot 78 sliding along guide pin 35, such that finger 72 is moved at an acute angle to the longitudinal axis to contact the crown portion of the distalmost staple. Finger 72 forces the individual staple along firing path 320 through the tissue and into anvil depressions 162 to bend the staple legs into a B-shaped configuration as best shown in FIG. 8.

After the firing stroke is complete, the trigger arm 52 is released, and trigger mechanism 60 returns to its normal distal position under the biasing force of tension spring 51. This longitudinal return motion of trigger mechanism 60 is transferred to actuating lever 80 via camming pin 58 sliding upwardly in angular cam slot 86, causing the actuating lever 80 to pivot to its original position shown in FIG. 4. This pivotal motion of actuating lever 80 is transferred to upward translation of pusher mechanism 70 (FIG. 8) as finger 82 slides distally in channel 73. Pusher 70 is consequently returned to its original retracted position wherein guide pin 35 of staple carrying arm 30 is seated in the lowermost portion of diagonal slot 78 and guide fastener 50 is seated in the lowermost portion of guide slot 79. Locking pin 46 of plate 45 is also carried distally by interlock 59 during the return motion of trigger mechanism 60 to re-engage locking groove 88 of actuating lever 80.

After firing of the staple and movement of finger 72 of pusher mechanism 70 out of the firing path 320, spring biased stack pusher 37 urges the stack of staples distally, (see arrow B in FIG. 9), so that the distalmost staple is forced into the firing path 320 in position to be contacted by the pusher mechanism 70 upon reactivation of trigger mechanism 60.

The handles 10, 30 are subsequently pivoted apart to open the jaws 14, 33 and the instrument is removed from the tissue. If desired, the jaws of the instrument can be re-clamped and additional staples applied to the surgical site by actuation of the trigger mechanism as described above.

Another embodiment of the surgical stapler of the present invention is illustrated in FIGS. 10–16, and is designated generally by reference numeral 2. This instrument is similar to the instrument of the first embodiment illustrated in FIGS. 1–9 in that the anvil carrying arm or handle 100 and the staple carrying arm or handle 130 operate in a scissor like fashion to clamp tissue between its distal jaws, and a separate trigger mechanism 160 fires the individual staple into the clamped tissue. This embodiment differs in that the trigger mechanism 160 is directly connected to the staple pusher and located on one side of the instrument. The pusher mechanism and cartridge of instrument 2 are similar to that of instrument 1 and therefore will not be discussed in detail.

Anvil carrying handle 100 and staple carrying handle 130 each terminate in finger loops 101,131 to be grasped by the user. Although not shown, a stop can be provided to limit closure of the handles as in instrument 1 of FIG. 1. The handle 100 includes an anvil jaw 114 at its distal end having a pair of depressions 118 to receive and bend the staple legs. Handle 130 terminates at its distal end with a jaw 132 for mounting a cartridge of the type described above. Staple pusher guide pin 134, secured to staple jaw 132, extends through a diagonal slot 172 in staple pusher 170. Staple pusher 170 includes a longitudinal channel 173 formed proximally of slot 172, and is slidably mounted to staple carrying arm 130 via central guide fastener 150 extending through a guide slot (not shown). Distal finger 178 is configured to advance the individual staples S.

Figure 11:
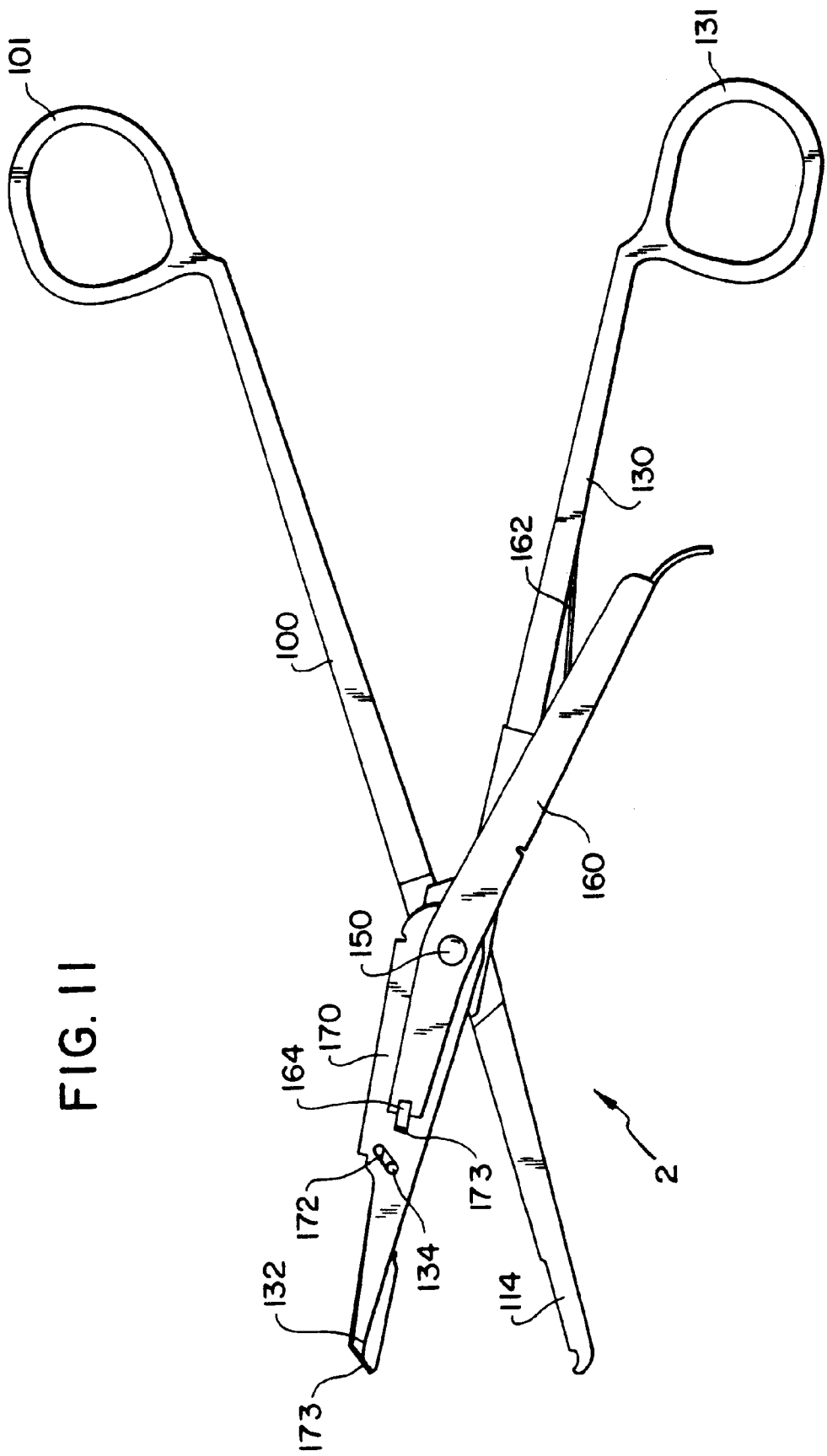
FIG. 11 is a side view of the apparatus of FIG. 10 shown with the tissue clamping jaws in the open position.

Referring to FIG. 11, trigger mechanism 160, mounted to handles 100, 130 by central fastener 150, includes a trigger spring 162 which biases it away from staple carrying handle 130. Finger 164 extends inwardly from trigger mechanism 160 into channel 173 and functions to slide staple pusher 170.

In operation, handles 100, 130 are squeezed together (FIG. 12) to close jaws 114, 132 around body tissue positioned therebetween. In this position, guide pin 134 and guide fastener 150 are seated in the lowermost positions of slot 172 and the guide slot (not shown), respectively. Once the tissue is securely clamped, trigger mechanism 160 is pressed towards handle 130 in the direction of arrow C of FIG. 13 to overcome the bias of trigger spring 162. Thus, staple pusher 170 translates downwardly in the direction of arrow D of FIGS. 13 and 15 due to the cooperation between inwardly extending finger 164 and channel 173. Finger 178 of staple pusher 170 consequently contacts the crown portion of the distalmost staple and advances it into the anvil depressions 118 for formation into a B-shaped configuration.

Figure 12:
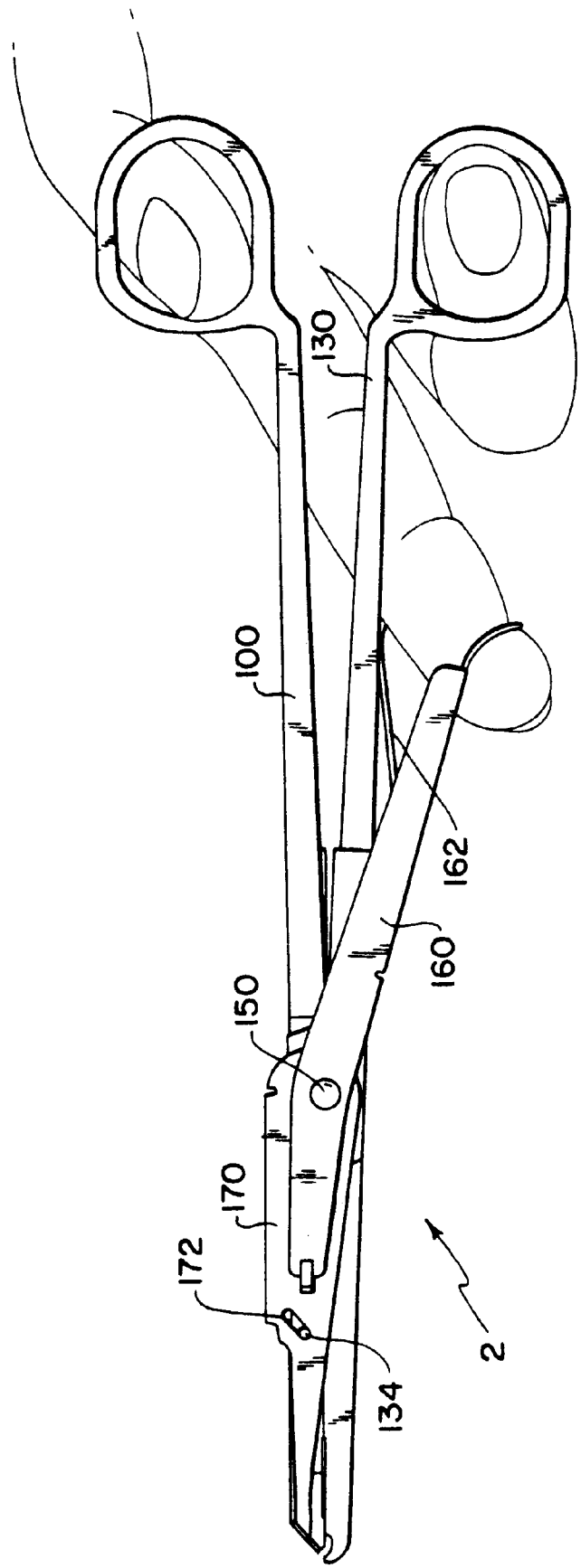
FIG. 12 is a side view of the apparatus shown with the tissue clamping jaws in the closed position and the staple pusher in the retracted, pre-fired position.
Figure 13:
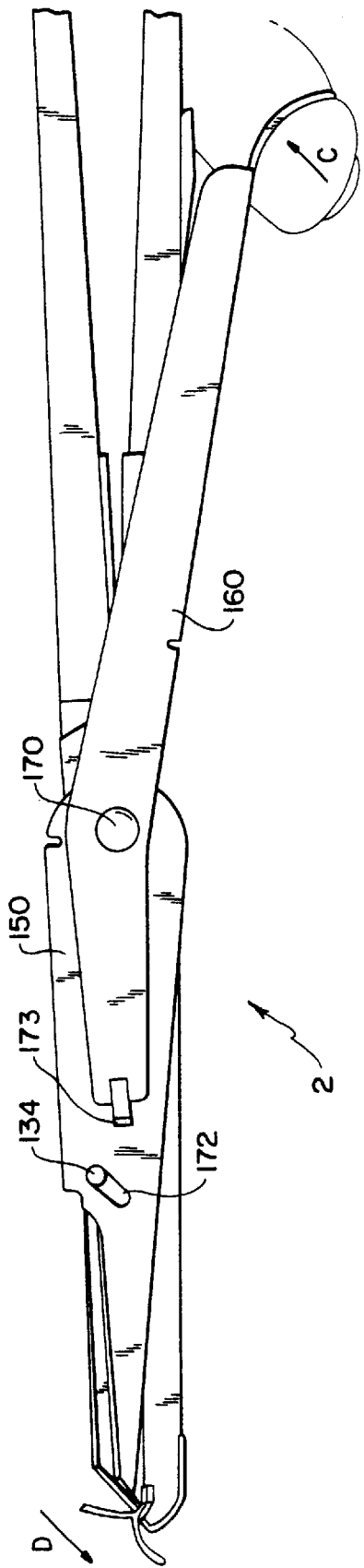
FIG. 13 is a side view of the apparatus shown with the tissue clamping jaws in the closed position and the stapler pusher in the advanced, fired position.
Figure 14:
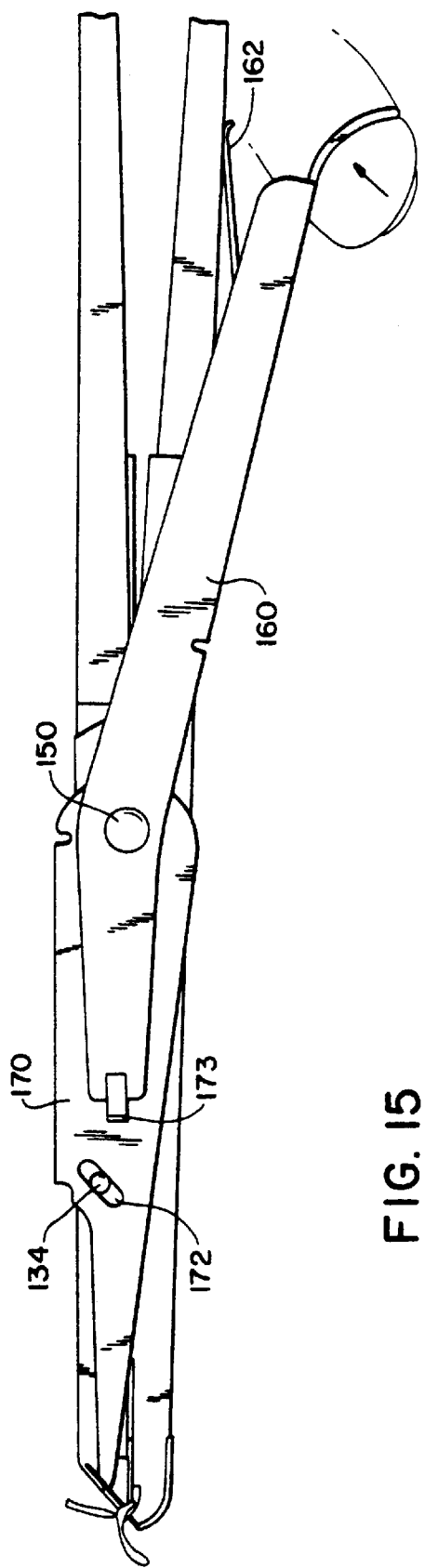
FIG. 14 is a side view of the apparatus showing a staple implanted in the body tissue and the staple pusher partially returned to its retracted position.
Figure 15:
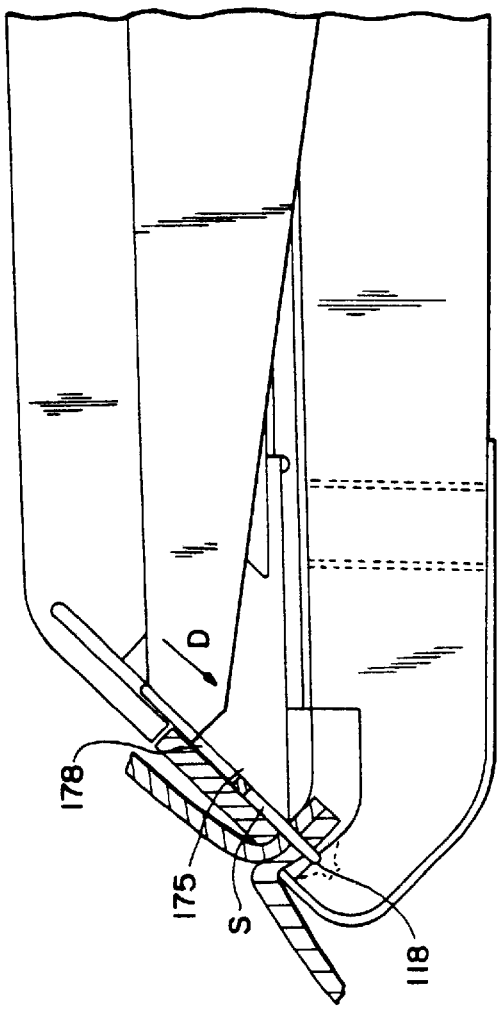
FIG. 15 is an enlarged view of the distal end of the apparatus showing the staple pusher being advanced to fire the staple.
Figure 16:
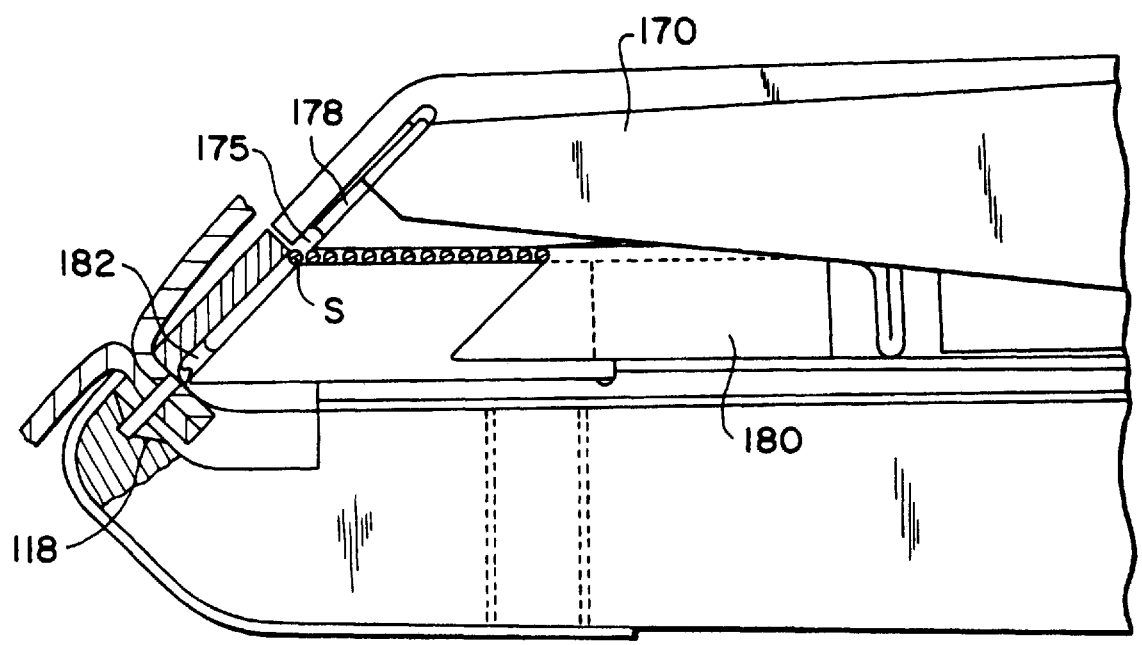
FIG. 16 is an enlarged view of the distal end of the apparatus showing a staple implanted in the body tissue and the staple pusher fully returned to its retracted position.

When trigger mechanism 160 is released, staple pusher 170 translates upwardly as shown in FIG. 14 and returns to its original position illustrated in FIG. 12. The stack of staples is urged distally by stack pusher 180 (FIG. 16) when finger 178 is retracted out of the firing path 175 such that the distalmost staple is moved into the firing path 175 in position for advancement upon reactivation of the instrument.

Note that the terms "upwardly", "downwardly", "lowermost", etc. used above are with reference to the illustrated orientation of the instrument. Clearly, if the instrument orientation changes, the corresponding directions will also change.

The instruments 1 and 2 of the present invention have particular application to vascular tissue, although they can be used to attach or close openings in other types of body tissue. The clamping and closing of individual vessels to effect hemostasis by the stapling apparatus of the present invention saves the surgeon valuable time. The stapling apparatus of the present invention can also be used to attach approximated vessels or vessel portions. In this procedure, the vessels are held in close apposition, and each leg of the staple is inserted through one of the vessels or vessel portions. The B-shaped formation of the legs provides advantageous attachment of the approximated vessels.

The instruments 1 and 2 of the present invention can also be used in laparoscopic or endoscopic procedures. That is, the instrument with its handles and jaws closed, can be inserted through a small incision in the body or through a narrow endoscopic tube which is positioned through a small opening in the skin and extends into the interior of the body. After insertion, the jaws can be opened and then closed around the body tissue. A staple can then be applied to the body tissue by manipulation of the trigger mechanism.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical stapling apparatus comprising:
    a first handle member having a first elongated jaw member at a distal end, said first jaw member having a staple-retaining member disposed thereon;
    a second handle member pivotally connected to said first handle member and having a second elongated jaw member at a distal end, said second jaw member having an anvil positioned thereon for forming a staple wherein relative movement of said first and second handle members results in corresponding relative movement of said first and second jaw members to move the jaw members from an open position to a closed position;
    a staple pusher adapted to advance said staples one at a time into contact with said anvil to secure tissue; and
    a trigger operatively connected to said staple pusher when the jaw members are in the closed position, said trigger being inoperatively associated with the staple pusher when the jaw members are in the open position, said trigger being moved from operative connection to inoperative association with the staple pusher in response to movement of the jaw members from the closed to the open position.

2. A surgical stapling apparatus as recited in claim 1, wherein said first and second elongated jaw members are integral with said first and second handle members, respectively.

3. A surgical stapling apparatus as recited in claim 2, wherein said first and second handle members are pivoted toward and away from each other to close and open said first and second elongated jaw members.

4. A surgical apparatus as recited in claim 2, wherein said trigger is attached to said second handle member.

5. A surgical apparatus as recited in claim 1, wherein said trigger is slidably mounted proximally of said staple pusher for movement between said first position and said second position to actuate said staple pusher.

6. A surgical apparatus as recited in claim 4, wherein said staple pusher is mounted over said first elongated jaw members.

7. A surgical apparatus as recited in claim 1 wherein said staple-retaining member comprises a cartridge mounted to said first jaw for carrying a plurality of staples.

8. A surgical apparatus as recited in claim 7, wherein said staples are stacked in said cartridge at an angle to a longitudinal axis of said second handle member.

9. A surgical apparatus as recited in claim 1, further comprising an actuating lever operatively associated with said trigger and said staple pusher.

10. A surgical apparatus as recited in claim 9, wherein said actuating lever is pivotally mounted to the apparatus for movement from a first position to a second position.

11. A surgical apparatus as recited in claim 7, wherein pivotal movement of said actuating lever to said second position advances said staple pusher into contact with a distalmost staple to form said staple against said anvil.

12. A surgical apparatus as recited in claim 11, wherein manual movement of said trigger pivotally actuates said actuating lever.

13. A surgical apparatus as recited in claim 9, wherein said actuating lever includes a cam slot and said trigger includes a pin extending into said cam slot, wherein movement of said trigger from said nonfiring position to said firing position causes said pin to travel in said cam slot to pivot said actuating lever.

14. A surgical apparatus as recited in claim 13, wherein said actuating lever includes means for engaging said staple pusher means, and said staple pusher includes a recess for receiving said engaging means.

15. A surgical stapling apparatus comprising:
a first handle defining a longitudinal axis and having a proximal end and a distal end having a first jaw;
a staple cartridge containing at least one staple mounted to said first jaw, said staple having a pair of legs joined by a crown portion;
a second handle having a proximal end with a mounting portion, and a distal end having a second jaw;
a pivot member connecting said first handle to said second handle whereby approximation of said first and second handles moves said jaws to a closed position to clamp body tissue therebetween;
at least one staple advancing member for advancing an individual staple into the body tissue after said first and second handles are pivoted to clamp body tissue, said at least one advancing member being pivotably mounted to said first and second handles;
an actuating lever operatively associated with said at least one staple advancing member and having angled camming structure, said actuating lever adapted to actuate said at least one staple advancing member;
a trigger having a first distal member and a second proximal member moveable by said first distal member through said angled camming structure, said trigger slidably mounted to said mounting portion of said second handle, said trigger being slidable along said longitudinal axis between a nonfiring position and a firing position wherein movement to said firing position moves said actuating lever to actuate said at least one staple advancing member, said trigger moveable when said jaws are in said closed position between said nonfiring position in which said advancing member is not actuated to said firing position in which said at least one staple advancing member is actuated;
a safety operatively associated with said trigger;
wherein said safety is mounted to prevent movement of said trigger from said nonfiring position to said firing position when said jaws are not in said closed position.

16. A surgical apparatus as recited in claim 15, wherein said staple cartridge includes a stack of staples aligned along a longitudinal axis of said first jaw.

17. A surgical apparatus as recited in claim 16, wherein the staple legs are positioned at an acute angle to a longitudinal axis of said second handle.

18. A surgical apparatus as recited in claim 15, wherein said staple cartridge is removably mounted to said first jaw.

19. An apparatus as recited in claim 18, further comprising a staple cartridge holder, said holder mounted to said first jaw and having a pair of rails to secure said staple cartridge therein.

20. A surgical apparatus as recited in claim 15, wherein said actuating lever is attached to said first and second handles.

21. A surgical apparatus as recited in claim 20, wherein said actuating lever includes a cam slot and an inwardly extending finger, said cam slot receiving a pin extending from said trigger and said finger extending into a channel in said at least one advancing member.

22. A surgical apparatus as recited in claim 21, wherein said trigger is spring biased in a distal position.

23. A surgical stapling apparatus comprising:
a first elongated jaw adapted to contain at least one staple, said first jaw having a handle portion;
a second elongated jaw for carrying an anvil, said second jaw having a handle portion;
a staple advancing member mounted to said first jaw for advancing a staple against said anvil;
a first pivot member connecting said first jaw to said second jaw whereby approximation of said handle portions of said first and second jaws moves said jaws to a closed position to clamp tissue therebetween;
at least one lever cooperating with said staple advancing member, said at least one lever having an extension received in a channel formed in said advancing member;
pivoting means for pivoting a second pivot member movable into engagement with said at least one lever, wherein pivotal movement of said at least one lever moves said staple advancing member into an advanced position to push the staple into contact with the anvil; and
a safety operatively associated with said second pivot member;
wherein said safety is mounted to prevent movement of said at least one actuating lever when said jaws are not in said closed position.

24. A surgical apparatus as recited in claim 23, wherein said staple advancing member defines a slot, said slot receiving a transverse pin fixed to said first jaw to restrict longitudinal movement of said advancing member.

25. A surgical apparatus as recited in claim 24, wherein said means for pivoting said lever includes a slidable trigger.

26. A surgical stapling apparatus comprising:
a first elongated jaw member having a first longitudinal axis;
at least one staple contained by said jaw member;
a second elongated jaw member having a second longitudinal axis and including an anvil, said anvil extending at an obtuse angle to said second longitudinal axis and having at least one depression configured to deform said staple;
means pivotably mounted to said first jaw member for advancing said staple into contact with said anvil when said jaw members have clamped body tissue therebetween, said advancing means movable in a direction which is at an angle to said first longitudinal axis and said advancing means being slidably mounted to said first jaw member for movement between a retracted position adjacent said first jaw member to a forward biased position and trigger means for actuating said advancing means, said trigger means having a projection engaging a channel formed in said advancing means.

27. A surgical apparatus as recited in claim 26, wherein said trigger means is spring biased away from said first and second said longitudinal axes of the apparatus.

28. A surgical stapling apparatus comprising:

a first handle member having a first elongated jaw at a distal end, said first jaw having a plurality of staples positioned thereon;

a second handle member having a second elongated jaw at a distal end, said second jaw having an anvil positioned thereon for forming the staples;

a pivot member connecting said first handle member to said second handle member whereby approximation of said first and second handle members move said first and second jaws to a closed position to clamp tissue therebetween;

a staple pusher which is adapted to advance said staples one at a time into contact with said anvil to secure the body tissue;

a trigger pivotably connected to said staple pusher and operable independently from said pivot member, said trigger moveable when said first and second jaws are in said closed position between a nonfiring position and a firing position to actuate the staple pusher; and a safety moveable into engagement with said trigger;

wherein when said first and second jaws are in said closed position movement of said trigger actuates said staple pusher;

wherein said safety prevents said trigger from moving said staple pusher when said first and second jaws are not in said closed position.

29. A surgical apparatus as recited in claim 28, wherein said trigger is disposed on an outer surface of the apparatus and spring biased away from said handle members.

30. A surgical stapling apparatus comprising:

a first elongated jaw member having a first longitudinal axis;

at least one staple contained by said jaw member;

a second elongated jaw member having a second longitudinal axis and including an anvil, said anvil extending at an obtuse angle to said second longitudinal axis and having at least one depression configured to deform said staple;

means pivotably mounted to said first jaw member for advancing said staple into contact with said anvil when said jaw members have clamped body tissue therebetween, said advancing means movable in a direction which is at an angle to said first longitudinal axis and said advancing means being slidably mounted to said first jaw member for movement between a retracted position adjacent said first jaw member to a forward biased position and trigger means for actuating said advancing means and lever actuating means linking said trigger means to said advancing means, said lever actuating means having a projection engaging a channel formed in said advancing means.

31. A surgical stapling apparatus comprising:

a first handle defining a longitudinal axis and having at least one staple positioned in a magazine at a distal end of said first handle;

a second handle having an anvil at a distal end, said first and second handles being relatively pivotable to move said anvil and said magazine between an open position and a closed position to clamp body tissue therebetween;

a staple pusher being movable to advance at least one staple from said magazine into contact with said anvil;

an actuator operatively associated with said pusher and having an angled camming portion formed thereon, said actuator adapted to actuate said pusher to advance the at least one staple; and a trigger assembly having a trigger slidably connected to said second handle, the trigger having a distal portion and a proximal portion, the distal portion being engageable with the angled camming portion in the closed position of said anvil and said magazine to facilitate actuation of the pusher, the distal portion being disengaged with the angled camming portion in response to movement of said anvil and said magazine to the open position of the jaws to prevent actuation of the pusher.

* * * * *